US012746257B2

(12) United States Patent
Kramer et al.

(10) Patent No.: US 12,746,257 B2

(45) Date of Patent: Sep. 29, 2026

(54) IRON SUPPLEMENT COMPOSITIONS AND METHODS OF USE THEREOF

(71) Applicant: ThermoLife International, LLC, Signal Hill, CA (US)

(72) Inventors: Ronald Kramer, Signal Hill, CA (US); Alexandros Nikolaidis, Nea Kallikratia (GR)

(73) Assignee: ThermoLife International, LLC, Signal Hill, CA (US)

( * ) Notice: Subject to any disclaimer, the term of this patent is extended or adjusted under 35 U.S.C. 154(b) by 0 days.

(21) Appl. No.: 19/067,509

(22) Filed: Feb. 28, 2025

(65) Prior Publication Data

US 2025/0195564 A1 Jun. 19, 2025

Related U.S. Application Data

(60) Division of application No. 17/889,244, filed on Aug. 16, 2022, now abandoned, which is a continuation of application No. PCT/US2022/040429, filed on Aug. 16, 2022.

(60) Provisional application No. 63/233,682, filed on Aug. 16, 2021.

(51) Int. Cl.

| | |
|---|---|
| ***A61K 33/26*** | (2006.01) |
| ***A61K 9/00*** | (2006.01) |
| ***A61K 9/20*** | (2006.01) |
| ***A61K 31/375*** | (2006.01) |
| ***A61K 36/21*** | (2006.01) |
| ***A61P 43/00*** | (2006.01) |

(52) U.S. Cl.

CPC ............ *A61K 33/26* (2013.01); *A61K 9/0056* (2013.01); *A61K 9/20* (2013.01); *A61K 31/375* (2013.01); *A61K 36/21* (2013.01); *A61P 43/00* (2018.01)

(58) Field of Classification Search

CPC ................................ A61K 33/26; A61P 43/00

See application file for complete search history.

(56) References Cited

U.S. PATENT DOCUMENTS

| | | | | |
|---|---|---|---|---|
| 1,916,983 | A | | 7/1933 | Mckee |
| 2,176,144 | A | | 10/1939 | Moskowitz |
| 2,553,533 | A | | 5/1951 | Komarik |
| 3,230,036 | A | | 1/1966 | Kappelmann |
| 3,552,978 | A | | 1/1971 | Inklaar |
| 3,886,040 | A | | 5/1975 | Chibata |
| 3,956,513 | A | | 5/1976 | Clarke |
| 3,997,659 | A | | 12/1976 | Knohl |
| 4,146,611 | A | | 3/1979 | Ondetti |
| 4,273,937 | A | | 6/1981 | Gum |
| 4,291,015 | A | | 9/1981 | Keith |
| 4,379,177 | A | | 4/1983 | Mccoy |
| 4,678,670 | A | | 7/1987 | Tomic |
| 4,687,782 | A | | 8/1987 | Brantman |
| 4,743,614 | A | | 5/1988 | Terano |
| 4,749,402 | A | | 6/1988 | Garrett |
| 4,871,550 | A | | 10/1989 | Millman |
| 4,976,960 | A | | 12/1990 | Grossman |
| 4,996,067 | A | | 2/1991 | Kobayashi |
| 5,026,071 | A | | 6/1991 | Miraglia, Jr. |
| 5,026,721 | A | | 6/1991 | Dudrick |
| 5,242,697 | A | | 9/1993 | Luca |
| 5,411,569 | A | * | 5/1995 | Hjersted .................. C05D 9/02 210/710 |
| 5,485,827 | A | | 1/1996 | Zapol |
| 5,500,436 | A | | 3/1996 | Schoenafinger |
| 5,543,430 | A | | 8/1996 | Kaesemeyer |
| 5,576,351 | A | | 11/1996 | Yoshimura |
| 5,631,031 | A | | 5/1997 | Meade |
| 5,679,704 | A | | 10/1997 | Schoenafinger |
| 5,767,160 | A | | 6/1998 | Kaesemeyer |
| 5,904,924 | A | | 5/1999 | Gaynor |
| 5,965,596 | A | | 10/1999 | Harris |
| 6,063,432 | A | | 5/2000 | Maxwell |
| 6,136,339 | A | | 10/2000 | Gardiner |
| 6,159,485 | A | | 12/2000 | Yu |
| 6,172,098 | B1 | | 1/2001 | Harris |
| 6,277,884 | B1 | | 8/2001 | de Tejada |
| 6,337,349 | B2 | | 1/2002 | Scafetta |
| 6,451,341 | B1 | | 9/2002 | Slaga |
| 6,562,869 | B1 | | 5/2003 | Hamilton |
| 6,608,109 | B2 | | 8/2003 | Allen |
| 6,784,209 | B1 | | 8/2004 | Gardiner |
| 7,040,313 | B2 | | 5/2006 | Fine |

(Continued)

FOREIGN PATENT DOCUMENTS

| | | |
|---|---|---|
| CN | 1056225 | 11/1991 |
| CN | 1049824 | 3/2000 |

(Continued)

OTHER PUBLICATIONS

Hurrell et al. The Usefulness of Elemental Iron for Cereal Flour Fortification: A SUSTAIN Task Force Report, Nutrition Reviews, Dec. 2002, pp. 391-406. (Year: 2002).*

(Continued)

*Primary Examiner* — Sarah Pihonak

*Assistant Examiner* — Mikhail O'Donnel Robinson

(74) *Attorney, Agent, or Firm* — Pacer K. Udall; Booth Udall, PLC

(57) ABSTRACT

The disclosure is directed to a method of replenishing a subject's iron, ferritin, and/or hemoglobin level. The method includes orally administering elemental metal iron to the subject; and orally administering a source of nitrate anion to the subject.

27 Claims, No Drawings

(56) References Cited

U.S. PATENT DOCUMENTS

| | | | |
|---|---|---|---|
| 7,235,237 | B2 | 6/2007 | Loscalzo |
| 7,777,014 | B2 | 8/2010 | Cattaruzza |
| 7,777,074 | B2 | 8/2010 | Kramer |
| 7,799,782 | B2 | 9/2010 | Munson |
| 8,034,836 | B2 | 10/2011 | Kramer |
| 8,048,921 | B2 | 11/2011 | Kramer |
| 8,178,572 | B2 | 5/2012 | Kramer |
| 8,183,288 | B2 | 5/2012 | Kramer |
| 8,303,995 | B1 | 11/2012 | Bryan |
| 8,455,531 | B2 | 6/2013 | Kramer |
| 8,466,187 | B2 | 6/2013 | Kramer |
| 8,569,368 | B2 | 10/2013 | Kramer |
| 8,569,369 | B2 | 10/2013 | Kramer |
| 8,703,719 | B1 | 4/2014 | Abraham |
| 8,852,660 | B2 | 10/2014 | Miljkovic |
| 8,952,045 | B1 | 2/2015 | Kramer |
| 8,952,046 | B1 | 2/2015 | Kramer |
| 8,957,100 | B1 | 2/2015 | Kramer |
| 8,957,101 | B1 | 2/2015 | Kramer |
| 9,180,140 | B2 | 11/2015 | Lundberg |
| RE46,372 | E | 4/2017 | Miller |
| 10,555,921 | B1 | 2/2020 | Kramer |
| 10,646,508 | B1 | 5/2020 | Kramer |
| 10,736,916 | B1 | 8/2020 | Kramer |
| 10,736,917 | B1 | 8/2020 | Kramer |
| 11,154,499 | B2 | 10/2021 | Nikolaidis |
| 11,260,096 | B2 | 3/2022 | Kramer |
| 11,865,139 | B2 | 1/2024 | Kramer |
| 2001/0002269 | A1 | 5/2001 | Zhao |
| 2001/0011074 | A1 | 8/2001 | Piccolo |
| 2001/0048952 | A1 | 12/2001 | Siskind |
| 2001/0055617 | A1 | 12/2001 | Mattern |
| 2001/0056069 | A1 | 12/2001 | Klaus |
| 2002/0006532 | A1 | 1/2002 | Robin |
| 2002/0022060 | A1 | 2/2002 | Mathur |
| 2002/0065323 | A1 | 5/2002 | Crooks |
| 2002/0119933 | A1 | 8/2002 | Butler |
| 2002/0136802 | A1 | 9/2002 | Mehansho |
| 2002/0147156 | A1 | 10/2002 | Petit |
| 2003/0012744 | A1 | 1/2003 | Pedersen |
| 2003/0014238 | A1 | 1/2003 | Xun |
| 2003/0062043 | A1 | 4/2003 | Fine |
| 2003/0091615 | A1 | 5/2003 | Craig |
| 2003/0097401 | A1 | 5/2003 | Bauman |
| 2003/0119888 | A1 | 6/2003 | Allen |
| 2003/0139354 | A1 | 7/2003 | Buccholz |
| 2004/0006140 | A1 | 1/2004 | Kaesemeyer |
| 2004/0048870 | A1 | 3/2004 | Amir |
| 2004/0057926 | A1 | 3/2004 | Ochoa |
| 2004/0058011 | A1 | 3/2004 | Petersson |
| 2004/0087518 | A1 | 5/2004 | Verlaan |
| 2004/0097401 | A1 | 5/2004 | Datta |
| 2004/0126366 | A1 | 7/2004 | Kaddurah-Daouk |
| 2004/0224868 | A1 | 11/2004 | Meyerhoff |
| 2004/0242682 | A1 | 12/2004 | Kaesemeyer |
| 2005/0043274 | A1 | 2/2005 | Murad |
| 2005/0043287 | A1 | 2/2005 | Allen |
| 2005/0053673 | A1 | 3/2005 | Netke |
| 2005/0171194 | A1 | 8/2005 | Yu |
| 2005/0196474 | A1 | 9/2005 | Anno |
| 2005/0256192 | A1 | 11/2005 | Gardiner |
| 2005/0261257 | A1 | 11/2005 | Vermeer |
| 2005/0287210 | A1 | 12/2005 | Ron |
| 2005/0288372 | A1 | 12/2005 | Ron |
| 2005/0288373 | A1 | 12/2005 | Ron |
| 2006/0014238 | A1 | 1/2006 | Gholap |
| 2006/0018281 | A1 | 1/2006 | Sadot |
| 2006/0029668 | A1 | 2/2006 | Ron |
| 2006/0035007 | A1 | 2/2006 | Kawabe |
| 2006/0063827 | A1 | 3/2006 | Yu |
| 2006/0116328 | A1 | 6/2006 | Babizhayev |
| 2006/0134227 | A1 | 6/2006 | Bortz |
| 2006/0142382 | A1 | 6/2006 | Morimoto |
| 2006/0182815 | A1 | 8/2006 | Gladwin |
| 2006/0188607 | A1 | 8/2006 | Schramm |
| 2006/0198899 | A1 | 9/2006 | Gardiner |
| 2006/0241181 | A1 | 10/2006 | Pola |
| 2006/0275909 | A1 | 12/2006 | Spitzer |
| 2007/0037880 | A1 | 2/2007 | Mailland |
| 2007/0105817 | A1 | 5/2007 | Page |
| 2007/0141174 | A1 | 6/2007 | Cornett |
| 2007/0154569 | A1 | 7/2007 | Gladwin |
| 2007/0166355 | A1 | 7/2007 | Brakstad |
| 2008/0004218 | A1 | 1/2008 | Quay |
| 2008/0026075 | A1 | 1/2008 | Kondo |
| 2008/0038410 | A1 | 2/2008 | Giordano |
| 2008/0138448 | A1 | 6/2008 | Heuer |
| 2008/0163793 | A1 | 7/2008 | Gernon |
| 2008/0214649 | A1 | 9/2008 | Yu |
| 2008/0233186 | A1 | 9/2008 | Romero |
| 2008/0233242 | A1 | 9/2008 | Zhang |
| 2008/0268095 | A1 | 10/2008 | Herzog |
| 2009/0076110 | A1 | 3/2009 | Kramer |
| 2009/0137670 | A1 | 5/2009 | Kramer |
| 2009/0182044 | A1 | 7/2009 | Ashmed |
| 2009/0280199 | A1 | 11/2009 | Russell |
| 2009/0306208 | A1 | 12/2009 | Shimada |
| 2010/0004335 | A1 | 1/2010 | Kagami |
| 2010/0047344 | A1 | 2/2010 | Lundberg |
| 2010/0092441 | A1 | 4/2010 | Lundberg |
| 2010/0172890 | A1 | 7/2010 | Gilad |
| 2011/0064712 | A1 | 3/2011 | Amato |
| 2011/0123654 | A1 | 5/2011 | Jaeger |
| 2012/0220643 | A1 | 8/2012 | Kramer |
| 2013/0011377 | A1 | 1/2013 | Perrin |
| 2013/0071494 | A1 | 3/2013 | Bryan |
| 2013/0101704 | A1 | 4/2013 | Meehan |
| 2015/0246066 | A1 | 9/2015 | Nelson |
| 2017/0042935 | A1 | 2/2017 | Sakamoto |
| 2017/0303582 | A1 | 10/2017 | Lu |
| 2017/0306440 | A1 | 10/2017 | Hein |
| 2018/0055879 | A1 | 3/2018 | Novak |
| 2018/0133247 | A1 | 5/2018 | Green |
| 2020/0222449 | A1 * | 7/2020 | Nikolaidis .............. A61P 21/00 |
| 2020/0275685 | A1 * | 9/2020 | Catanese .............. A61K 31/375 |
| 2020/0405662 | A1 | 12/2020 | Kramer |
| 2021/0220422 | A1 | 7/2021 | Parker |
| 2021/0355191 | A1 | 11/2021 | Sherman |
| 2022/0143080 | A1 | 5/2022 | Kramer |

FOREIGN PATENT DOCUMENTS

| | | | |
|---|---|---|---|
| CN | 1631539 | | 6/2005 |
| CN | 20041009958 | | 6/2005 |
| CN | 109480107 | | 3/2019 |
| CN | 110680809 | | 1/2020 |
| CR | 20140504 | A2 | 3/2015 |
| EP | 0031284 | | 7/1981 |
| EP | 0454396 | | 10/1991 |
| EP | 797992 | | 1/1997 |
| EP | 1336602 | | 8/2003 |
| EP | 1429829 | | 11/2013 |
| EP | 2896302 | | 7/2015 |
| GB | 1089084 | | 11/1967 |
| GB | 2008578 | | 6/1979 |
| GB | 2052976 | | 2/1981 |
| GB | 2354441 | | 3/2001 |
| JP | 2010519335 | | 6/2010 |
| JP | 2012529909 | | 11/2012 |
| JP | 2014513527 | | 6/2014 |
| JP | 2014122162 | | 7/2014 |
| KR | 20110015141 | | 2/2011 |
| WO | 9843499 | | 10/1998 |
| WO | 0040217 | | 7/2000 |
| WO | 0117525 | | 3/2001 |
| WO | 0195897 | | 12/2001 |
| WO | 03063789 | | 8/2003 |
| WO | 2005062713 | | 7/2005 |
| WO | 2005115175 | A1 | 12/2005 |
| WO | 2006025286 | | 3/2006 |
| WO | 2006124161 | | 11/2006 |
| WO | 2007000985 | | 1/2007 |
| WO | 2007066642 | | 6/2007 |
| WO | 2007093808 | | 8/2007 |

(56) References Cited

FOREIGN PATENT DOCUMENTS

| | | | |
|---|---|---|---|
| WO | 2008009615 | 1/2008 | |
| WO | 2008043855 | 4/2008 | |
| WO | 2008105730 | 9/2008 | |
| WO | 2008105731 | 9/2008 | |
| WO | WO-2012094598 A2 * | 7/2012 | ............ A61K 47/52 |
| WO | 2018019663 | 2/2018 | |
| WO | 2018071988 | 4/2018 | |
| WO | 2020160509 | 8/2020 | |
| WO | 2020214841 | 10/2020 | |
| WO | 2021188163 | 9/2021 | |
| WO | 2022104157 | 5/2022 | |
| WO | 2022192743 A1 | 9/2022 | |

OTHER PUBLICATIONS

Lundberg et al., Arterioscler. Thromb. Vase. Biol., 25:915-922 (2005).
Lundberg, "Inorganic Nitrate is a Possible Source for Systemic Generation of Nitric Oxide," Free Radical Biology & Medicine,vol. 37, No. 3, pp. 395-400, 2004.
Marconi, Int. J. Sports Med, 11 (1990):1-14.
Material Safety Data Sheet—Taurine, 5 pages. Print date Aug. 28, 2009.
Miller, Elements of Chemistry—Theoretical and Practical, Longsmans, Green, Reader and Dyer, 1869, pp. 757-770.
MrSupplement.com product dietary supplement Creatine Nitrate, 2006. 2 pages.
Muramoto, J., "Comparison of Nitrate Content in Leafy Vegetables from Organic and Conventional Farms in California" Center for Agroecology and Sustainable Food Systems University of California, Santa Cruz, 1999. 66 pages.
Nature's Best advertisement for "Perfect L-Glutamine" Joe Weider's Muscle & Fitness, Sep. 2005. 2 pages.
NutraBioBCAA2500, 2006. 1 page.
Optimum Nutrition advertisement for "Adenergy Stack" Joe Weider's Muscle & Fitness, Sep. 2005. 2 pages.
Pariser et al. Curtis, 1994, 54(1): 43-44 respectively.
Parker et al., The Effect of Supplemental L-Arginine on Tolerance Development During Continuous Transdermal Nitroglycerin Therapy, J. of Am. Coll. of Cardiology, 39(7): 1199-1203, 2002.
PEScience High Volume, 2007. 2 pages.
Petersson et al., "Dietary nitrate increases gastric mucosal blood flow and mucosal defense," Am. J. Physiol. Gastrointest. Liver, 292: G718-G724, 2007.
Piccolo et al. CAS: 138: 1375892003. 3 pages. 2014.
Pickering et al., Why Don't We Use Nitrates to Treat Older Hypertensive Patients?, Journal of Clinical Hypertension, vol. 7, No. 11, pp. 685-690 (Nov. 2005).
Pischel et al. CAS: 134:71896, 2001. 1 page.
ProArgi 9 Supplement Website: ProArgi-9 Plus FAQ, "ProArgi 9 Plus Site", http:// proargi9site.blogspot.eom/p/proargi-9-plus-faq.html, Apr. 22, 2014. 5 pages.
UDINTSEV. Nitrates and physical performance. Siberian fiber. Aug. 9, 2018. [on-line] [ retrieved on Jun. 29, 2020] (Retrieved from the Internet: https://tfzp.rU/zdorovyj-obraz-zhizni/v/nitraty/ nitraty-i-fizicheskaya-rabotosposobnostO, p. 2, paragraph 2-p. 3, paragraph 1, p. 4, paragraph 1.
PS Nutrition Creatine Nitrate, on line, sale product, 2014. 5 pages.
QuadraLean by RSP Nutrition, Bodybuilding.com, 2006. 1 page.
Harris, R.C., "The Influence of Beta-Alanine Supplementation and Training on the Muscle Carnosine Content in Human v. lateralis, and the Effect of This on Exercise Performance," Amino Acids 29:12-13 (2005).
Rajkumar et al., "Infrared and Raman spectra of DL-aspartic acid nitrate monohydrate," Spectrochimica Acta Part A, 54:1527-1532, 1998.
Riens et al., "Amino Acid and Sucrose Content Determined in the Cytosolic, Chloroplastic, and Vacuolar Compartments and in the Phloem Sap of Spinach Leavesl", Plant Physiol. (1991) 97, 227-233, Apr. 6, 1991.
Rimando et al., "Determination of Citrulline in Watermelon Rind", Journal of Chromatography A, 1078 (2005) 196-200, May 2, 2005.
Rombauer, Irma S., "Joy of Cooking", 75th Anniversary, Scribner, New York, 2006, p. 163 (2006).
Rosen et al. "Nutrient Management for Commercial Fruit & Vegetable Crops in Minnesota" University of Minnesota extension Service, 2005 pp. 35-36 <https://conservancy.umn.edu/bitstream/handle/11299/51272/5886.pdf?sequence=1>.
RSPReGenBCAA, 2006. 2 pages.
Moncada et al., "The L-Arginine: Nitric Oxide Pathway", Journal of Cardiovascular Pharmacology, 17(Suppl. 3):S1-S9, Raven Press, New York, 1991.
S. Ramaswamy, Acta Cryst., E58, 646-648 (2002).
Sader et al., "Endothelial Function, Vascular Reactivity and Gender Differences in the Cardiovascular System", Cardiovascular Research 53 (2002) 597-604, Aug. 21, 2001.
Sale et al. Effect of beta-alanine supplementation on muscle carnosine concentrations and exercise performance. Amino Acids, 39:321-333, 2010.
San Corporation dietary supplement containing creatine nitrate, 2006. 1 page.
Santamaria et al. "A survey of nitrate and oxalate content in fresh vegetables" Journal of the Science of Food and Agriculture, 1999, vol. 79, 1882-1888. (Year: 1999).
Sastre et al., "Metabolism of agmatine in macrophages: modulation by lipopolysaccharide and inhibitory cytokines," Biochem. J. 330:1405-1409 (1998).
Schaefer et al. publication, Inti. J. of Sports Medicine, 2002,23(6):403-407.
Schulbach et. al., "Guide to nitrogen quick-tests for vegetables wit the 'cardy' nitrate meter" FREP Contract #95/0582. 11 pages.
Sen et al.Journal of Association of Official Analytical Chemists, 61(6): 1389-1394, 1978.
Shen et al. publication, Acta Physiol. Scand, 2000, 168(4): 675-86.
Shen et al., "Nitric oxide production and NO synthase gene expression contribute to vascular regulation during exercise.", Med Sci Sports Exerc, 27(8):1125-34, 1995.
Simplico et al. "Prodrus for Amines", Molecules 2008, vol. 13, pp. 519-547.
Srinivasan et al., "L-phenylalanine-nitric acid (2/1)," Acta Crystallographica E57:o916-o918, 2000.
Stephany et al. "The intake of nitrate, nitrite and volatile N-nitrosoamines and the occurrence of volatile N-nitrosamines in human urine and veal calves", IARC Scientific Publications, Jan. 1978, vol. 19, pp. 443-460 (Year: 1978).
Stephenson, Terence, "How children's responses to drugs differ from adults," Br. J. Clin. Pharmacol. 59(6): 670-673, Jun. 2005.
Stetson, C, "Characteristics of Adults vs. Children." [retrieved on May 4, 2016]. Retrieved from the Internet <URL: ittp://www.ehow.com/info 8501147 characteristics-adults-vs-children.html>.
Stout et al., "Effects of B-Alanine Supplementation on the onset of Neuromuscular Fatigue and Ventilatory Threshold in Women", Amino Acids (2006), Springer-Verlag 2006. 6 pages.
Stryer, Lubert, Biochemistry, Third Edition, W.H. Freeman and Company, New York: 1988, pp. 15-24, 233-236, 261-268, 499-502 and 933-936.
Sugino et al., "L-ornithine supplementation attenuates physical fatigue in healthy volunteers by modulating lipid and amino acid metabolism," Nutrition Research, 2008, 28:738-743.
Summary of Studies of B-Alanine and sports performance, "Studies of B-Alanine Supplementation on Exercise Capacity or Performance", Nov. 2011. 5 pages.
Swensen et al. publication, Intl. J. of Sports Medicine, 1994, 15(7):430-4.
Godzisz, "Classification and nature of hydrogen bonds to betaine. X-ray, 13C CP MAS and IR description of low barriei hydrogen bonds," Journal of Molecular Structure, 606:123-137,2002.
Green et al. publication, Sports Med., 1996, 21(2): 119-146.
Gwartney, D. L, "On the Horizon: Agmatine," Oct./Nov. 1998, PUMP 101:96-97.
Harris et al. "The absorption of orally supplied beta-alanine and its effect on muscle carnosine synthesis in human vastus lateralis" Amino Acids, 2006, vol. 30, pp. 270-289. (Year: 2006).

(56) References Cited

OTHER PUBLICATIONS

Harrison, D.G. et al., "The Nitrovasodilators, new Ideas About Old Drugs," Circulation, vol. 87, No. 5, May 1993, pp. 1461-1467).
Haussuhl, "Elastic and thermoelastic properties of twelve adducts of betaine," Z Kristallogr, 188:311-320, 1989.
Henriksson et al, Acta Physiol, Sep. 1, 2007, 191:1. 1 page.
Herbwisdom.com, 2006. 4 pages.
Hoffman et al., "Effect of Creatine and p-Alanine Supplementation on Performance and Endocrine Responses in Strength/Power Athletes", International Journal of Sport Nutrition and Exercise Metabolism, 2006, 16, 430-446, © 2006 Human Kinetics, Inc.—20.
Honikel's publication, Meat Science, 2008,78: 68-76.
Hord et al., "Food Sources of Nitrates and Nitrites: The Physiological Context for Potential Health Benefits," Am. J. Clin. Nutr. 90:1-10, 2009.
http://www.beyondsupplements.com.au/index.php?route=product/, no date given. 5 pages.
http://www.bodybuilding.com/store/fuel-one/6th-gear.html, no date given. 4 pages.
http://www.curezone.org, no date given. 5 pages.
http://www.dymatize.com/store/workoutsupport/M-P-ACT-Energy, no date given. 4 pages.
http://www.ergo-log.com/plaatjes/xpand2x.gif, no date given.
https://nuts.com/cookingbaking/powders/beet.html, 2016.
https://www.thesynergycompany.com/organic-carrot-juice-powder, no date given.
Shi et al. , Handbook of Food Science, Technology, and Engineering, vol. 4, 2006, Chapter 170, p. 170-5.
Hunter et al., "The Inhibition of Arginase By Amino Acids", Department of Pathological Chemistry, University of Toronto, Canada, Jul. 24, 1944. 20 pages.
Huxtable et al. Physiological Reviews, 72(1):101-142, 1992.
IForce Nutrition product "Potassium Nitrate", 2006. 2 pages.
Ignarro ("After 130 years, the molecular mechanism of action of nitroglycerin is revealed," [online], Jun. 11, 2002 [retrieved on May 8, 2016]. Retrieved from the Internet: <http://www.pnas.Org/cgi/content/full/99/12/7816?ck=nck>). 28 pages.
Ignarro et al. publication, The Journal of Pharmacology and Experimental Therapeutics, 1988., 244(1): 181-189.
Ignarro et al., "Pharmacology of Endothelium-derived Nitric Oxide and Nitrovasodilators", The Western Journal of Medicine, Jan. 1991, 154. 9 pages.
Ilczyszyn et al. CAS: 145:83630 2006. 2 pages.
Ingested Nitrate and Nitrite, and Cyanobacterial Peptide Toxins, World Health Organization International Agency for Research on Cancer (2010) 24 pages.
Ionic Liquids ( URL: https://www.organic-chemistry.org/topics/ionic-liquids.shtm ), printed Apr. 2019 (Year: 2019). 4 pages.
J. Abrams, MD, Beneficial Actions of Nitrates in Cardiovascular Disease, The American Journal of Cardiology, vol. 77, pp. 31C-37C (May 30, 1996).
Jamalian et al., "Nutritional Value of Middle Eastern Foodstuffs", Jamalian & Pellett: Nutritional Value of Middle Eastern Foodstuffs. IV, Dec. 1967. 5 pages.
Joy et al., "A multi-ingredient, preworkout supplement is apparently safe in healthy males and females," Food & Research, 59:27470, 2015, 7 pages.
Cosby et al., "Nitrite reduction to nitric oxide by deoxyhemoglobin vasodilates the human circulation", Nature Medicine, vol. 9, No. 12, Dec. 2003. 9 pages.
K. Tsuchiya, et al., Malfunction of Vascular Control in Lifestyle-Related Diseases: Formation of Systemic Hemoglobin-Nitric Oxide Complex (HbNO) From Dietary Nitrite, J. Pharmacol Sci, vol. 96, pp. 395-400 (2004).
Kemmerer et al. publication, J. Nutr., 1949, 38(4): 527-33.
Kendrick et al., "The effect of 4 weeks B-alanine supplementation and isokinetic training on carnosine concentrations in type 1 and II human skeletal muscle fibres", Eur J Appl Physiol (2009) 106:131-138, Feb. 12, 2009.
Kenechuwu et al. J. Microencapsul, 2017, 34(6):592-609.
Kernohan et al., "An oral yohimbine/L-arginine combination (NMI 861) for the treatment of male erectile dysfunction: a pharmacokinetic, pharmacodynamic and interaction study with intravenous nitroglycerine in healthy male subjects", British Journal of Clinical Pharmacology, © 2004 Blackwell Publishing Ltd. 9 pages.
Kou et al. application No. 200410009958.3, 2005. 27 pages.
Kramer et al., U. S. Patent Application Publication No. 2009/076110 A1 published Mar. 19, 2009. 12 pages.
Appel et al., "A Clinical Trial of the Effects of Dietary Patterns on Blood Pressure", The New England Journal of Medicine, 336(16): 1117-1124, 1997.
L. Brunton, An Address on Blood Pressure In Man: Its estimation and indications for treatment, The British Medical Journal, pp. 64-67 (Jul. 10, 1909).
L. Brunton, et al., An Address on Longevity and the Means of Attaining It, The Lancet, vol. 168, Issue 4342, pp. 1330-1335 (Nov. 17, 1906).
L. Noah et al, Starting from Scratch?: Reinventing the Food Additive Approval process, Boston Univ. L. Rev. vol. 78:329, pp. 329-443 1998.
Large Wendy, "Circuit training combines aerobic and anaerobic workouts into one," News Journal (Mansfield Ohio), Sep. 5, 2004. 3 pages.
Larsen, Effects of dietary nitrate on blood pressure in healthy volunteers, New England Journal of Medicine 355:2792-2793 (2006).
Lewis et al. publication, Pharmacol. Biochem Behav, 2007, 88(1): 114-21.
Ilczyszyn et al. 13C chemical shift tensors of hydrogen bonded amino acids: Relations between experimental and calculated results. Chemical Physics 323 (2006) 231-242.
Luigi et al., Med. Sci Sports Exerc, 1999, 31(12): 1748-54.
Lundberg et al., "Cardioprotective effects of vegetables: Is nitrate the answer?", Science Direct, Jan. 2006. 4 pages.
Lundberg et al., "The nitrate-nitrite-nitric oxide pathway in physiology and therapeutics", Nat Rev Drug Discov., 7 (2):156-167, 2008.
Ruel et al., "Modulation in Angiogenic Therapy randomized controlled trial," J Thorac Cardiovasc Surg 135:762-770 (2008).
Material Safety Data Sheet—agmatine sulfate salt, 2008. 3 pages.
Material Safety Data Sheet-L-Arginine. 5 pages. Print date Aug. 26, 2009.
Material Safety Data Sheet—beta-alanine. 5 pages. Print date Aug. 26, 2009.
Material Safety Data Sheet-L-Glutamine. 2008. 6 pages.
Material Safety Data Sheet-L-Leucine MSDS. 6 pages. Created 2005.
Material Safety Data Sheet-L-Norvaline. 2 pages. Date unknown.
"Isosorbide dinitrate—leaflet print—Patient UK," available at http://www.patient.co.uk/printer.asp?doc= 30003884, 2011.
"Isosorbide mononitrate-leaflet print—Patient UK," available at http://www.patient.co.uk/printer.asp?doc=30003885, 2008.
"Dietary Nitrate and Nitrite to Increase Nitric Oxide in Patients with Coronary Artery Disease," Clinical Trial available at http://clinicaltrials.gov/ct2/show/NCT00069654, 2010.
"Dymatize Nutritional Supplements, Whey Protein, Bodybuilding & Weight Products", 2013 Dymatize Enterprises LLC, Xpand 2×36 Serving, http://www.dymatize.com/products/nitric-oxide/detail/1166/ xpand-2x-36-serving, 2013. 4 pages.
"Heart attack—Nitrates & vasodilators—Revolution health," available at http://www.revolutionhealth.com/conditions/heart/heart-attack/medication-types/nitrates-vasodilators, 2011. 1 page.
"Nitrates and nitrites (PIM G016)," available at http://inchem.org/documents/pims/chemical/img016.htm, retrieved online Mar. 23, 2011.
"Nitrates and Nitrites", TEACH Chemical Summary, U.S. EPA, Toxicity and Exposure Assessment for Children's Health, published by the U.S. Environmental Protection Agency on May 22, 2007 (Year: 2007). 15 pages.
"Xpand 2x by Dymatize at Bodybuilding.com—Lowest Price on Xpand 2x!", Advertisement, 2012 BodyBuilding.com, LLC, http://www.bodybuilding.com/store/dymatize/xpand-2x.html, Jun. 8, 2013. 5 pages.

(56) References Cited

OTHER PUBLICATIONS

FDA 21 C.F.R. (I)(B) §§ 172.160 and 172.170, revised Apr. 1, 2018 (Year: 2018). 12 pages.
A Butler et al., Medieval Chinese Medicine: The Dunhuang Medical Manuscripts (Chapter 16: A treatment for carenovascular dysfunction in a Dunhuang medical manuscript), Routledge (2005) 14 pages.
Abd El-Gawad et al. AAPS PharmaSciTech, 2017, 18(5):1795-1809.
Abou-Mohamed et al. "Role of L-Arginine in the Vascular Actions and Development of Tolerance to Nitroglycerin", British Journal of Pharmacology (2000) 130, 211-218.
Amidon, G. L. et al., "Intestinal Absoption of Amino Acid Derivatives: Structural Requirements for Membrane Hydrolysis.", Journal of Pharmaceutical Sciences., (1983), vol. 72, No. 8, pp. 943-944, XP055127041.
Amino Thrust dietary supplement, 2007. 2 pages.
Anders et al. "Aminoacylases", 1994, Advances in Pharmacology, vol. 27, pp. 431-448. (Year: 1994).
Anderson, K. "Nitrate and Nitrite in Human Nutrition" The Graduate College in the University of Nebraska, Lincoln, Nebraska, 1982. 160 pages.
Archer, Douglas L., Evidence that Ingested Nitrate and Nitrite Are Beneficial to Health, Journal of Food Protection, vol. 65, No. 5, pp. 872-875 (2002).
Arenas et al., Muscle & Nerve, 1991,14:589-604.
Arnold Iron CRE3, 2007. 1 page.
Artioli et al. "Role of beta-Alanine Supplementation on Muscle Carnosine and Exercise Performance" Med. Sci. Sprots Exerc, Jun. 2010, vol. 42, No. 6pp. 1162-1173.
Atanasova, Plant Siol Environ, 2008, 54(2):66-71.
ATSDR Case Studies in Environmental Medicine Nitrate/Nitrite Toxicity published by the U.S. Department of Health and Human Services on Dec. 5, 2013. ATSDR Case Studies in Environmental Medicine Nitrate/Nitrite Toxicity. 135 pages.
Avraham et al., "Tyrosine improves appetite cognition and exercise tolerance in activity anorexia," Medicine & Science in Sports & Exercise, 33(12): 2104-2110, 2001.
B. C. Challis, Nutrition and nitrosamine formation, Proceeds of the Nutrition Society, vol. 44, pp. 95-100 (1985).
B. Spiegelhalder, et al., Influence of Dietary Nitrate On Nitrate Content of Human Saliva: Possible Relevance of N-Nitroso Compounds, Fd. Cosmet. Toxicol., vol. 14, pp. 545-548 (1976).
Bahadur et al., "Crystal and molecular stucture of DL-aspartic acid nitrate monohydrate," Z. Kristallogr. 210: 276-278, 1995.
Bailey et al. "Dietary nitrate supplementation reduces the 02 cost of low-intensity exercise and enhances tolerance to ligh-intensity exercise in humans", J. Appl. Physiol., 2009, vol. 107, pp. 1144-1155. (Year 2009).
Baran, "Crystal structure, phase transitions and vibrational spectra of bis(betaine) nitrate," Journal of Molecular Structure, 372:131-144, 1995.
Barger et al., Monographs on Biochemistry, 1914, The Simpler Natural Bases, pp. 157-163.
Barron JT and Parillo JE, "Production of lactic acid and energy metabolism in vascular smooth muscle: effect of dichloroacetate." Am J Physiol. Feb. 1995;268(2 Pt 2): H713-9.
Basheva et al., "Role of Betaine as Foam Booster in the Presence of Silicone Oil Drops," Langmuir 16:1000-1013 (2000).
BeetV02Max—max Nitric Oxide Booster, Amazon.com, 2006. 1 page.
D. Bendahan et al., "Citrulline/Malate Promotes Aerobic Energy Production in Human Exercising Muscle," Br. J. Sports Med. 36:282-89 (2002).
Benjamin, Nigel, Nitrates in the Human Diet—good or bad?, Ann. Zootech. vol. 49, pp. 207-216 (2000).
Betancourt product: Betancourt Ripped Juice EX2, 2006. 3 pages.
Blodgett et al. "Incidence of Hematologic Disease in Patients with Carpal Tunnel Syndrome" JAMA, 1962, 182(7), pp. 814-815.
Bloomer et al., "Comparison of pre-workout nitric oxide stimulating dietary supplements on skeletal muscle oxygen saturation, blood nitrate/nitrite, lipid peroxidation, and upper body exercise performance in resistance trained men", Journal of the International Society of Sports Nutrition 2010, 7:16, http://www.jissn.com/content/7/1 /16. 15 pages.
Boguslavskiy. Effect of nitric oxide on the efficiency of oxygen usage by a working skeletal muscle under fatigue, Fiziol. Zhum., vol. 51, No. 1, pp. 33-42 (2005) & Certified Translation.
Borison et al., "Brain 2-phenylethylamine as a major mediator for the central actions of amphetamine and methylphenidate," Life Sci. 17: 1331-1344, Nov. 1975.
Bover-Cid et al., "Biogeneic Amine Accumulation in Ripened Sausages Affected by the Addition of Sodium Sulphite", Meat Science 59 (2001) 391-396, Mar. 20, 2001.
Bryan, Nathan S., Food, Nutrition and the Nitric Oxide Pathway, Biochemistry and Bioactivity, pp. 59-63, DESTech Publications, Inc., Lancaster PA, (2010).
BSN Volumaize Aretic Blast, on line, sale product, 2014. 1 page.
Burtscher. The Proonged Intake of L-Arginine-L-Aspartate Reduces Blood Lactate Accumulation and Oxygen Consumption During Submaximal Exercise, Journal of Sports Science and Medicine, vol. 4, pp. 314-322 (2005).
B. Pejin et al., Heavy metal content of a medicinal moss tea for hypertension, Natural Product Research, Taylor & Francis, 2012 vol. 26, No. 23, 2239-2242.
B. Pejin et al., Mineral Content of a Moss Tea for Hypertention, Italian Journal of Food Science , Italy Codon Publications, 2013 vol. 25, 235-237.
Carbonyl diamine [online] retrieved on Aug. 18, 2023 from: https://www.chembk.com/en/chem/Carbonyl%20diamine; 1 page. (Year: 2023).
Galachiev S.M. et al: Possibilities of endogenous formation of nitrosamines in gastric juice In Vitro, Samara Scientific Center of the Russian Academy of Sciences Bulletin, 2011, vol. 13, No. 1(7), pp. 1678-1680.
Kumar et al., "Chemical Denitrificaiton of Water by Zero-Valent Magnesium Powder." Journal of Hazardous Materials, vol. 135, No. 1-3, Jul. 31, 2006, pp. 112-121.
Magnesium, Britannica Online Encyclopedia [online] retrieved on May 30, 2024 from: https://www.britannica.com/print/article/356899; 3 pages.) (Year: 2024).
Mirvish, S.S., "Blocking the formation of N-nitroso compounds with ascorbic acid in vitro and in vivo," Annals of New York Academy of Sciences. 1975; pp. 175-180) (Year: 1975).
Raymond et al., "Effects of Acute Red Spinach Extract Ingestion on Repeated Sprint Performance in Division I NCAA Female Soccer Athletes." (Oxygen 2023;3:133-142). (Year: 2023).
Vilskersts. R. et al. Magnesium nitrate attenuates blood pressure rise in SHR rats. Magnes Res. Jan.-Mar. 2014; 27 (1):16-24. doi:10.1684/mrh.2014.0358. PMID: 24827813.
Zhang X, et al. Effects of Magnesium Supplementation on Blood Pressure: A Meta-Analysis of Randomized Double- Blind Placebo-Controlled Trials. Hypertension. Aug. 2016;68(2):324-33. doi: 10.1161/HYPERTENSIONAHA.116.07664. Epub Jul. 11, 2016. PMID: 27402922.
Que, R. et al., "A Simple, Facile Demonstration of Copper and Nitric Acid Reaction", Journal of Chemical Education. 2022, 99, 2762-2765.
Lakhmir Singh ([online] retrieved on Dec. 18, 2024 from: https://www.google.com/books/edition/Lakhmir_Singh_s_Science_for_Class_8/ z2wtDAAAQBAJ?hl=en&gbpv=0; 2016; p. 70) (Year: 2016).
Hyde, PJ et al., "The Reaction Between Aluminum Metal and Aqueous Solutions of the Nitrite Ion", Austalian Journal of Chemistry, vol. 33, No. 1, Jan. 1, 1980 (Jan. 1, 1980), p. 169, XP093223550, AU, ISSN:0004-9425, DOI: 10.1071/CH9800169.
Body S. C. et al., "Nitric Oxide: Delivery, Measurement, and Clinical Application", Journal of Cardiothoracic and Vascular Anesthesia, Elsevier, Amsterdam, NL, vol. 9, No. 6, Jan. 1, 1995, pp. 748-763, XP009009779, ISSN: 1053-0770, DOI: 10.1016/S1053-0770(05)80242-3.

(56) References Cited

OTHER PUBLICATIONS

Zapol, Warren M. et al., "Inhaled Nitric Oxide", British Journal of Pharmacology, Dec. 31, 2019, pp. 246-255, XP093223242, DOI: 10.1111/bph.v176.2/issuetoc.
U.S. Department of Commerce, "The Atmosphere", National Oceanic and Atmospheric Administration , retrieved on Nov. 13, 2024, https://www.noaa.gov/jetstream/atmosphere.
Astill, B. D. et al., "Phenolic Antioxidants amd the Inhibition of Hepatotoxicity from N-Dimethylnitrosamine Formed in Situ in the Rat Stomach" Food and Cosmetics Toxicology, Pergamon Press, Oxfrod, Grat Britain, vol. 15, No. 3, Jan. 1, 1977, pp. 167-171.
Gui, Iai et al., "Reduction of N-Nitrosodimethylamine with Granular Iron and Nickel-Enhanced Iron. 1. Pathways and Kinetics", Environmental Science & Technology, vol. 34, No. 16, Jul. 14, 2000, pahes 3489-3494.
Westerhoff P. et al., "Nitrate removal in zero-valent iron packed columns", Water Research, Elsevier, Amsterdam, NL, vol. 37, No. 8, Apr. 1, 2003 (Apr. 1, 2003), pp. 1818-1830, XP004419942, ISSN: 0043-1354, DOI: 10.1016/S0043-1354(02)00539-0.
Zhang Z. et al., "Reductive denitrification kinetics of nitrite by zero-valent iron", Desalination, Elsevier, Amsterdam, NL, vol. 257, No. 1-3, Jul. 1, 2010 (Jul. 1, 2010), pp. 158-162, XP027020374, ISSN: 0011-9164.
Han Ying et al., "Reduction of N-Nitrosodimethylamine with zero-valent zinc", Water Research, vol. 47, No. 1, Jan. 1, 2013 (Jan. 1, 2013), pp. 216-224, XP093221894, Amsterdam, NL ISSN: 0043-1354, DOI: 10.1016/j.watres.2012.09.043.
English translation of patent CR 20140504 A2; Dec. 4, 2015.
Sheiner et al., "Pharmacokinetic/Pharmacodynamic Modeling in Drug Development", Annu. Rev. Pharmacol. Toxicol., vol. 49, pp. 67-95. 2000.
Oldreive, C, Rice-Evans, C, "The Mechanisms for Nitration and Nitrotyrosine Formation in vitro and in vivo: Impact of Diet", Free Rad. Res., vol. 35, pp. 215-231, 2001.
CAS Registry No. 89695-59-0 https://chem.nlm.nih.gov/chemidplus/m/89695-59-0, 1984. 1 page.
Cavassa et al. W098/43499. International Publication Date: Oct. 8, 1998. 33 pages.
Chemical Abstracts Service, "Chemical Abstracts", The American Chemical Society, Liquid Crystals, vol. 104, Jun. 2, 1986. 2 pages.
ColorMaker, 2006. 1 page.
CPG Sec 565.100 FDA Jurisdiction Over Meat and Poultry Products, 2005. 3 pages.
Craig, Betaine in human nutrition, 1 Am J Clin Nutr, 80:539-549,2004.
Creatine from Wikipedia, 2017. 2 pages.
Creatine nitrate from PubChem, 2017. 1 page.
Cromwell et al., "The Biosynthesis and Metabolism of Betaines in Plants," 1953 Biochem J., 55: 189-192.
Crooks et al., U. S. Patent Application Publication No. 2002/0065323 A1, published May 30, 2002. 8 pages.
Curtis, J., Dec. 6, 2017, "Nitrate-Free Bacon: Myth or Reality", https://firsthandfoods.com/author/jennifer/, pp. 1-2 Year: 2017).
D. D. Rees, et al., Role of endothelium-derived nitric oxide in the regulation of blood pressure, Proc. Natl. Acad. Sci. USA, vol. 86, pp. 3375-3378 (May 1989).
Danov et al., "Mixed Solutions of Anionic and Zwitterionic Surfactant (Betaine): Surface Tension Isotherms, Adsoprtionand Relaxation Kinetics," Langmuir 20:5445-5453 (2004).
Del Compo et al., "Creatinine, creatine and protein in cooked meat products", Food Chemistry, vol. 63, No. 2, pp. 187Y190, 1998.
Del Pilar Garcia-Santos et al., "Reactivity of Amino Acids in Nitrosation Reactions and Its Relation to the Alkylating Potential of Their Products," J. Am. Chem. Soc, 2002, 124(10): 2177-2182.
Dessaignes, "Research on Some Products of the Transformation of Creatine, "The Chemist—A Monthly Journal, vol. 1, Samual Highley Publishers, London, 1854, pp. 594-597.
Dhar et al., Complex Compounds of Acid, Base and Salt with Nitrogenous and Other Organic Substances, in National Academy of Sciences, India, Symposium on Nitrogen, Part 1, Section A, vol. 31, 1961, pp. 76-79.
Dhas, S.A. Martin Britto et al., Growth and Characterization of a New Organic NLO Material; Glycine Nitrate, ScienceDirect, Optics communications 278 (2007) 434-438.
Di Pasquale, Amino Acids and Proteins for the Athlete: The Anabolic Edge, 1st Edition, 1997, pp. 99-153.
Duncan et al., "Chemical generation of nitric oxide in the mouth from the enterosaliary circulation of dietary nitrate," Nature Medicine, 1 (6): 546-551, Jun. 1995.
Dymatize Nutrition, "Pre-Workout", http://www.dymatize.com/nitric-oxide, Mar. 31, 2014—Advertisement. 1 page.
Dymatize Nutrition, "Xpand 2x 10 Serving—Dymatize Nutritional Supplements, Whey Protein, Bodybuilding", http://www.dymatize.com/store/p/289-Xpand-2x-10-Servings.html-Advertisement. 2 pages.
Dymatize® Xpand 2x®, Fruit Punch, Dymatize—GNC, www.gnc.com/product/index.jsp?productId=13180805, Jun. 17, 2013, p. 1.
EAS advertisement for "Phosphagen Elite" Joe Weider's Muscle & Fitness, Sep. 2005. 2 pages.
Eaton et al., "Urinary Beta-Alanine Excretion is a Marker of Abnormal as well as Normal Gut Fermentation", Journal of Nutritional & Environmental Medicine (Jun. 2004) 14(2), 121-127.
Edwards et al., "Amino Acids in Foods, Cysteine, Tyrosine and Essential Amino Acid Contents of Selected Foods," Journal of Agriculture and Food Chemistry, 3(11):952-957, 1955.
Elkayam et al. "Prevention of nitrate tolerance with concomitant administration of hydralzaine" Can J CArdiol, 1996, vol. 12, suppl C, pp. 17C-21C. (Year 1996).
Elmore et al., "Compilation of free amino acid data for various food raw materials, showing the relative contributions of asparagine, glutamine, aspartic acid and glutamic acid to the fee amino acid composition", Oct. 2002, JIFSAN Acrylamide in Food Workshop, Chicago. (Year 2002). 3 pages.
English translation of KR-20110015141-A, Feb. 15, 2011, pp. 1-23 (Year: 2011).
Eppendorfer et al., "Free and Total Amino Acid Compositions of Edible Parts of Beans, Kale, Spinach, Cauliflower and Potatoes as influenced by Nitrogen," Journal of Science of Food and Agriculture, 71:449-458, 1996.
Eto et al. publication, Archives of Physiology and Biochemistry, 1995, 103(2):160-4.
Examine.com, "L-Carnitine", Sep. 12, 2014, https://examine.com/supplements/l-carnitine/. (Year:2014) 36 pages.
F. Murad, Cyclic Guanosine Monophosphate as a Mediator of Vasodilation, J. Clin. Invest., vol. 78, pp. 1-5 (Jul. 1986).
F. Ray, Meat Curing, ANSI-3994, OSU, 3 pages. Date unknown.
Fanous, S. "Is Sodium Nitrate Bad for You?", May 20, 2015, Healthline, https://www.healthline.com/health/food-iuthtion/is-sodium-nitrate-bad-for-you#1, pp. 1-8. (Year: 2015).
FDA Regulation 42 FR, 1977, 52 pages.
FDA Regulation 48 FR 1701, Indirect Food Additives; Paper and Paperboard Components, FDA, 1983, 5 pages.
Feelisch et al., Eur J. Pharmacol., 1987, 139(1): 19-30.
Flaherty, 1989, Drugs, 137:523-550.
Fraser et al., Circulation, 1983, 67(2): 405-412.
G. M. McKnight, et al., Chemical synthesis of nitric oxide in the stomachfi-om dietary nitrate in humans, Gut, vol. 40, pp. 211-214 (1997).
McKnight et al., "Review article: Dietary nitrate in man: friend or foe?", British Journal of Nutrition, 81:349-358, 1999.
G. R. J. Thatcher, Serial Review: Mechanisms and Novel Directions in the Biological Applications of Nitric Oxide Donors, Free Radical Biology & Medicine, vol. 37, No. 8, pp. 1122-1143 (2004).
Richardson et al., "The ingestion of inorganic nitrate increases gastric S-nitrosothiol levels and inhibits platelet function in humans", Nitric Oxide, 7:24-29, 2002.
Stokes et al., "Long-Term Effectiveness of Extended-Release Nitrate for the Treatment of Systolic Hypertension", Hypertension, 45:380-384, 2005.
Gao et al., "Agmatine: A Novel Endogenous Vasodilator Substance," Life Sciences, 57(8):83-86, 1995.

(56) References Cited

OTHER PUBLICATIONS

Giant Sport Metabolic Bioshock—Workout Supplement, on line, sale product, 2014. 1 page.
Gibson et al. "Protective role of the epithelium of the small intestine and colon", Inflamm. Bowel Dis., 1996, vol. 2, No. 1, pp. 279-302, abstract provided. (Year 1996).
GNC Mega Men, "GNC Mega Men 90 Caplets", http://www.gnc.com/GNC-Mega-Men-reg/ product.jsp?productId=4033432, Apr. 22, 2014. 3 pages.
Bhatia A.L., Jain Manish, "Amaranthus paniculatus (Linn.) improves learning after radiation stress", Journal of Ethnopharmacology, Elsevier Ireland Ltd, IE, IE , (20030301), vol. 85, No. 1, doi: 10.1016/S0378-8741(02)00337-9, ISSN 0378-8741, pp. 73-79, XP093036506.
Hu, "A Study on Elemental Irons and Iron Compounds for Food Fortification", 18th International Congress of Nutrition, pp. 1-9, Sep. 2005.
Mostad et al."Crystal and molecular structure of DL-methionine nitrate," CAS 104:197543 (1986). 1 page.
Pradhan et al."Effect of Anions on the Solubility of Zwitterionic Amino Acids," J. Chem. Eng. Data 45(1):140-143 (2000).
Luscher, "Endogenous and exogenous nitrates and their role in myocardial ischaemia," Br. J. Clin. Pharmacol. 34:29S-35S (1992).
Slart et al., "Nitrate Administration Increases Blood Flow in Dysfunctional but Viable MyocardiumLeading to Improved Assessment of Myocardial Viability: A PET Study," J. Nucl. Med. vol. 47: 1307-1311 (2006).
Schulz et al., "Functional and Biochecical analysis of Endothelial (Dys)function and NO/cGMP Signaling in Human Blood Vessels with and Without Nitroglycerin Pretreatment," Circulation 105:1170-1175 (2002).
Bauer et al., "Vascular and Hemodynamic Differences Between Organic Nitrates and Nitrites," Journal of Pharmacology and Experimental Therapeutics 280:326-331 (1997).
Ramaswamy et al., "Vibrational Spectroscopic Studies of L-argininium dinitrate" Journal of Raman Spectroscopy 2003. p. 50-56. vol. 34. www.interscience.wiley.com.
Rajkumar et al., "Infrared and Raman spectra of L-valine nitrate and L-leucine nitrate," J. Raman Spectrosc. 51:1107-1112(2000).
Petrosyan et al, "L-Histidine nitrates", Journal of Molecular Structure, 2006. p. 160-167 vol. 794. www.sciencedirect.com.
Jablecka et al., "The influence of two different doses of L-arginine oral supplementation on nitric oxide (NO) concentration and total antioxidant status (TAS) in atherosclerotic patients," Med Sci Monit 10(1):CR29-32 (2004).
Maynard et al."High Levels of Dietary Carnosine are Associated With Increased Concentrations of Carnosine and Histidine in Rat Soleus Muscle," J. Nutr. 131:287-290 (2001).
Rytlewski et al., "Effects of oral L-arginine on the pulsatility indices of umbilical artery and middle cerebral artery in preterm labor," European Journal of Obstetrics &Gynecology and Reproductive Biology 138:23-28 (2008).
Schwedhelm et al., "Pharmacokinetic and Pharmacodynamics properties of oral L-citrulline and L-arginine: impact on lithe oxide metabolism," Br J Clin Pharmacol 65(1):51-59 (2007).
Smith et al., "Nitric oxide precursors and congenital heart surgery: A randomized controlled trial of oral citrulline," J. Thorac Cardioasc Surg 132:52-65 (2006).
Rytlewski et al."Effects of prolonged oral supplementation with L-arginine on blood pressure and nitric oxide synthesis in preeclampsia," Eur J Clin Invest 35(1):32-37 (2005).
Ming et al., "Thrombin Stimulates Human Endothelial Arginase Enzymatic Activity via RhoA/ROCK Pathway," Simulation 110:3708-3714 (2004).
Romero et al."Therapeutic Use of Citrulline in Cardiovascular Disease," Cardiovascular Drug Reviews 24 (3-4):275-290 (2006).
Oka et al."A pilot study of L-arginine supplementation on functional capacity in peripheral arterial disease," Vascular Medicine 10:265-274 (2005).
Hayashi et al., "L-citrulline and L-arginine supplementation retards the progression of high-cholesterol-diet-induced atherosclerosis in rabbits," PNAS 102(38): 13681-13686 (2005).
Grasemann et al., "Oral L-arginine supplementation in cystic fibrosis patients: a placebo-controlled study," Eur Respir J 25:62-68 (2005).
Boger, "The Pharmacodynamics of L-Arginine," J. Nutr. 137:1650S-1655S (2007).
Beghetti et al. "Nitric oxide precursors and congenital cardiac surgery: A randomized controlled trial of oral citrulline. Definition of pulmonary hypertension in Fontan circulation?" J Thorac Cardioasc Surg 132(6): 1501-1502 (2006).
Berge et al., "Pharmaceutical Salts," Journal of Pharmaceutical Sciences 66(1):1-18 (1977).
Takahashi et al., "Characterization of the influence of nitric oxide donors on intestinal absorption of macromolecules," International Journal of Pharmaceutics 286:89-97 (2004).
Fetih et al., "Nitric oxide donors can enhance the intestinal transport and absorption of insulin and [Asu1,7]-eel Calcitonin in rats," Journal of Controlled Release 106:587-297 (2005).
Fetih et al. "Excellent Absorption Enhancing Characteristics of NO Donors for Improving the Intestinal Absorption of Poorly Absorbable Compund Compared with Conventional Absorption Enhancers," Drug Metab. Pharmacokinet. 21 (3):222-229 (2006).
Aniya et al., "Evaluation of Nitric Oxide Formation from Nitrates in Pig Coronary Arteries," Jpn. J. Pharmacol. 71:101-107 (1996).
Shiraki et al., "The hypotensive mechanisms of the new anti-anginal drugN-(2-Hydroxyethyl) Nicotinamide Nitrate (SG-75) in beagle dogs," Japan. J. Pharmacol. vol. 31:921-929 (1981).
CFIndustries, "Material Safety Data Sheet for Urea Ammonium Nitrate Solution (UAN)," available at www.cfindustries.com/pdf/UANMSDS.pdf Oct. 25, 2006. 13 pages.
Fayers et al."Nitrate tolerance and the links with endothelial dysfunction and oxidative stress," Br J Clin Pharmacol 56:620-628 (2003).
Knot, "Nitrate Tolerance in Hypertension: New Insight Into a Century-Old Problem," Circ Res 93:799-801 (2003).
Hatanaka et al., "Stereoselective Pharmacokinetics and Pharmacodynamics of Organic Nitrates in Rats," Journal of Pharmacology and Experimental Therapeutics 298:346-353 (2001).
Chabot et al., "Characterization of the vasodilator properties of peroxynitrite on rat pulmonary artery: role of poly (adenosine 5'-diphosphoribose synthase," British Journal of Pharmacology 121: 485-490 (1997).
Niu et al., "Vasorelaxant effect of taurine is diminished by tetraethylammonium in rat isolated arteries," European Journal of Pharmacology 580:169-174 (2008).
Tan et al."Taurine protects against low-density lipoprotein-induced endothelial dysfunction by the DDAH/ADMA pathway," Vascular Pharmacology 46:338-345 (2007).
Ahtee et al."Taurine Biological Actions and Clinical Perspectives," J. Nutr. 116:2555-2556 (1986).
Larsen et al., "Effects of Dietary Nitrate on Oxygen Cost During Exercise," Acta Physiol. 191: 59-66, 2007.
Bloomer et al., "Glycine propionyl-L-carnitine increases plasma nitrate/nitrite in resistance trained men," Journal of the International Society of Sports Nutrition 4(22):1 1-6 (2007).
"Glyceryl trinitrate—leaflet print—Patient UK," available at http://www.patient.co.uk/printer.asp?dock=30003883, 2008.
Xu et al., "Composite medical preparation for promoting hair growth," CAS: 143:103285 (2005). 1 page.
Peterosyan et al., "L-Hisitidine nitrates," J. Molecular Structure, 794: 160-167, 2006.
Sridhar et al, "L-Aspartic Acid Nitrate-L-Aspartic Acid," Acta Cryst. E58:01372-01374 (2002) 1 page.
B. Sridhar, et al, "Bis (beta-alanine) Hydrogen Nitrate", Acta Crystallographica Section, 2001, pp. 1004-1006 vol. 57.
Rao et al."Structure and Conformational Aspects of the Nitrates of Amino Acids and Peptides. I. Crystal Structure of Glycylglycine Nitrate," Acta Cryst. B29:2379-2388 (1973).
Bauer JA, et al, "Photochemical Generation of Nitric Oxide from Nitro-containing Compounds: Possible Relation to Vascular Photorelaxation Phenomena", Life Science, 1994, 54, 1PL 1-4.

(56) References Cited

OTHER PUBLICATIONS

Chang et.al. Arginase Modulates Nitric Oxide Production in Activated Macrophages. Am. J. Physiol., 1998, H342-H348.
Magg et al."Nitrogenous Compounds in Sugarbeet Juices," Journal of the American Society of Sugar Beet Technologists 17(2):154-164 (1972).
Tannebaum et al., "Inhibition of nitrosamine formation by ascorbic acid," Am. J. Clin. Nutr. 53: 2475-2505, 1991.
Tao, Guo-Hong et al., New Generation lonic Liquids: Cations Derived From Amino Acids, The Royal Society of chemistry, ChemComm, Jun. 9, 2006, 3562-3564.
Taurine from Nutrabio, 2006. 3 pages.
Teragawa et al. (Heart, 86:212-216, 2001) Magnesium causes nitric oxide independent coronary artery vasodilation in humans.
Terzyan et al., "L-Arginine Nitrates," Journal of Molecular Structure 687:111-117 (2004).
Thandani, U. "Challenges with Nitrate Therapy and Nitrate Tolerance: Prevalence, Prevention, and Clinical Relevance" Am J Cardiovasc Drugs, 2014, vol. 14, pp. 287-301. (Year: 2014).
The product APS Creatine Nitrate , for sale, 2014. 1 page.
The product Isoleucine nitrate power with a Brand name Hobid, for sale, 2014. 1 page.
The product L-glutamine nitrate power with a Brand name Hobid, for sale, 2014. 1 page.
The product L-Leucine nitrate power by Body Ripped, for sale, 2014. 1 page.
The product valine nitrate power with a Brand name Hobid, for sale, 2014. 1 page.
U.S. Food & Drug Administration document with respect to 21 CFR §184. 1878 for thiamine mononitrate (Year: 2018) 2 pages.
Urakami, M. et al., "Relationship between Structure and Permeability of Tryptophan Derivatives Across Human Intestinal Epithelial (Caco-2) Cells.", Z. Naturforsch., (2003), vol. 58C, pp. 135-142, XP055127040.
USDA and HHS Agencies Work Together to Examine the Jurisdiction of Certain Food Categories, USDA & FDA, 2005, 2 pages.
USDA Regulation 64 FR 72168, Food Ingredients and Sources of radiation Listed or Approved for Use in the Production of Meat and Poultry, 1999, 28 pages.
Vandenberghe et al. publicaiton, J. Appl physiol, 1997, 83:2055-2063.
Kouzenkov V.S. et al., "Sodium potassium effect on development of nerological deficiency in experimental model of brain ischemia", Moscow University Bulletin Ser. 16. Biology, (20140000), vol. 4, pp. 9-14, XP055831436.
Vytech advertisement for "Nitrobol Extreme" Joe Weider's Muscle & Fitness, Sep. 2005. 2 pages.
Walker et al., Food additive and Contaminants, 1990, 7(6):717-768.
Watt et al., "The Chemist, A Monthly Journal of Chemical & Physical Science", vol. 1, London; Samuel Highley, 32 Fleet Street, 1854. 5 pages.
Watts, "A Dictionary of Chemistry and the Allied Branches of Other Sciences", Library of the University of California, Aug. 1808. 5 pages.
Weitzberg et al., "Dietary Nitrate—A Slow Train Coming", J Physiol 589.22 (2011) pp. 5333-5533, 2011 The Authors. Journal compilation, 2011 The Physiological Society.
Wheatley et al., "Arginine deprivation and tumour cell death arginase and its inhibition," Molecular and Cellular Biochemistry, 244:177-185, 2003.
White, Handler and Smith, Principles of Biochemistry, Fifth Edition, McGrawy-Hill, New York: 1973, pp. 89-95.
Wilson et al., "Beta-Alanine-Bad Ass Supplement", Iron Man Magazine, Oct. 13, 2010. 14 pages.
Winter et al., "N-Nitrosamine Generation From Ingested Nitrate Via Nitric Oxide in Subjects With and Without Gastroesophageal Reflux," Gastroenterology, 2007, 133:164-174.
Ximenes et al. "Polarographic determination of nitrate in vegetables" Talanta, 2000, vol. 51, pp. 49-56. (Year: 2000).
Zhang et al. "Role of Taurine Supplementation to Prevent Exercise-Induced Oxidative Stress inhealthy Young Men" Amino Acids, 2004, 26:203-207.
Zhu et al., "Expression of Human Arginine Decarboxylase, the Biosynthetic Enzyme for Agmatine", NIH Public Access, Biochim Biophys Acta. Jan. 22, 2004; 1670(2): 156-164.
Ziegenfuss et al., "Effect of a Supplement Containing Primarily Beta Alanine, Arginine, Creatine Malate, and Glycerol Monostearate on Exercise-Induced Changes in Lean Mass of the Arms", Journal of the International Society of Sports Nutrition 2008, 5(Suppl 1):P16 doi: 10.1186/1550-2783-5-S1-P16. 2 pages.
Merriam-Webster definition of "dietary supplement" https://www.merriam-webster.com/dictionary/dietary%20supplement [accessed Jun. 20, 2019] (Year: 2019) 10 pages.
Beverly International advertisement, Joe Weider's Muscle & Fitness, Dec. 1987. 5 pages.
Mostad, A., "Crystal and molecular structure of DL-methionine nitrate," Zeitschrift fur Kristallographie, 172: 175-182, 1985.
Merriam-Webster definition of supplement https://www.merriam-webster.com/dictionary/ supplementlaccessed Jun. 20, 2019] (Year: 2019) 13 pages.
Gwartney, "On the Horizon: A Glimpse into the Future of Supplementation," in Pump magazine, Nov./Dec. 1998 4 pages.
Ishii et al., "High glucose augments arginase activity and nitric oxide production in the renal cortex," Metabolism 53 (7):868-874 (2004).
Arnold et al. (Biochemistry 99;38(15):4750-4756) (Year: 1999) 7 pages.
Yu, Qin, et al., "Portable Nitric Oxide (NO) Generator Based on Electrochemical Reduction of Nitrite for Potential Applications in Inhaled NO Therapy and Cardiopulmonary Bypass Surgery" Mol Pharm, vol. 14, No. 11, Nov. 6, 2017, pp. 3762-3771, XP055963565.
Shinbo, T. et al., "Breathing nitric oxide plus hydrogen gas reduces ischemia-reperfusion injury and nitrotyrosine production in murine heart", American Journal of Physiology-Heart and Circulatory Physiology, vol. 305, No. 4, 2013, p. H542, XP055189621, DOI: 10.1152/ajpheart.00844.2012.
Curry, M.D., Steven, "Methemoglobinemia", Ann Emerg Med, 11, 214-221, 1982.
A. Patrician et al., "Dietary nitrate enhances arterial oxygen saturation after dynamic apnea", Scand J Med Sci Sports, (20170000), vol. 27, doi: 10.1111/sms.12684, pp. 622-626, XP055943939.
H. Yamasaki, "Blood nitrate and nitrite modulating nitric oxide bioavailability: potential therapeutic functions in COVID-19", Nitric Oxide, vol. 103, doi:https://doi.org/10.1016/j.niox. Jul. 2020.00 5, (Jul. 23, 2020), pp. 29-30, XP055943941.
Sulcius, A. (J. Chem. Educ. 2015;92:1971-1972). (Year: 2015) 6 pages.
Gonzalez, "Migraines Are Correlated with Higher Levels of Nitrate-, Nitrite-, and Nitric Oxide-Reducing Oral Microbes in the American Gut Project Cohort". mSystems. Oct. 18, 2016;1(5):e00105-16. doi: 10.1128/mSystems.00105-16. Erratum in: mSystems. ( Year: 2016) 4 pages.
Ekblom et al., The new England Journal of Medicine, 2006, 335; 26, pp. 2792-2793.
Dymatize® Xpand 2x®, Fruit Punch, Dymatize GNC, www.gnc.com/product/index.jsp?productld=13180805, Jun. 13, 2013. 4 pages.
Gago et al., Red wine-dependent reduction of nitrite to nitric oxide in the stomach, Free Radical Biology and Medicine 43:1233-1242, 2007. 10 pages.
Acetyl/propionyl Carnitine from BodyBuilding, 2006.1 page.
George Barger, M.A., D.Sc., "The Simpler Natural Bases", Monographs on Biochemistry, U.C.D. Library, Nov. 23, 1960, Digitized 2007. 232 pages.
Ashenhurst ([online] retrieved on Aug. 18, 23 from: https://www.masterorganicchemistry.com/2018/02/28/ amides-properties-synthesis-and-nomenclature/ 3 pages) (Year: 2023).
"Co-administration" Cambridge English Dictionary; [online] retrieved on Mar. 27, 2025 from: https://dictionary.cambridge.org/us/dictionary/ english/co-administration; 1 page. (Year: 2025).
"Coadministration" Collins English Dictionary; [online] retrieved on Mar. 27, 2025 from: https://www.collinsdictionary.com/us/dictionary/ english/coadministration; 1 page. (Year: 2025).

(56) References Cited

OTHER PUBLICATIONS

Chauhan et al., "Advancements in the Co-Formulation of Biologic Therapeutics", Journal of Controlled Release, 2020;327:397-405. (Year: 2020).
Chen Zhonglin, "Efficacy of Zero-valentZinc in Reducing Edema with Trace Nitrosodimethylamine," Journal of harbin Institute of technology, vol. 42, No. 12, pp. 1879-1882. Dec. 31, 2010.
Food and Agriculture Organization, Technology of production of edible flours and protein products from soybeans, Chapter 1, "The Soybean", pp. 1-12, publ. Jan. 31, 2001 (Year: 2001).
Hanson et. al., Plant Physiol., vol. 70, pp. 1191-1198, publ. 1982 (Year: 1982).
Santamaria, J. of the Science of Food and Agriculture, vol. 86, pp. 10-17, publ. Nov. 1, 2005 (Year: 2005).
Wu Chun et al., "Study on the Inhibition of Nitrosamine Synthesis by Quercetin-Zinc(II) Complexes in Vitro and In Vitro," Food Science, vol. 28, No. 9, pp. 35-38. Dec. 31, 2007.
Kolb, Louis et al., "Oral Nitrate Increases Microvascular Reactivity and the No. of Visible Perfused Microvessels in Healthy Volunteers." Journal of Vascular Research, 2017, vol. 54, p. 209-216.
Alvarez Roger A. et al: "Home Nitric Oxide Therapy for COVID-19", American Journal of Respiratory and Critical Care Medicine, vol. 202, No. 1, Jul. 1, 2020 (Jul. 1, 2020), pp. 16-20, XP093325276, ISSN: 1073-449X, DOI: 10.1164/rccm.202005-1906ED.
Michele Umbrello et al: "The Key Role of Nitric Oxide in Hypoxia: Hypoxic Vasodilation and Energy Supply-Demand Matching", Antioxidans & Redox Signaling, vol. 19, No. 14, Nov. 10, 2013 (Nov. 10, 2013), pp. 1690-1710, XP055558805, US ISSN: 1523-0864, DOI: 10.1089/ars.2012.4979.
Anonymous: "Nitric oxide", Nov. 2, 2020 (Nov. 2, 2020), XP093325297, Retrieved from the Internet: URL:https://en.wikipedia.org/w/index.php?title=Nitric_oxide&oldid=986690656.
Do Amaral Angélica et al: "The effect of acute magnesium loading on the maximal exercise performance of stable chronic obstructive pulmonary disease patients", Clinics, vol. 67, No. 6, Jun. 1, 2012 (Jun. 1, 2012), pp. 615-621, XP093325270, BR ISSN: 1807-5932, DOI: 10.6061/clinics/2012(06)12.
Tang Chuan-Feng et al: "Possibility of magnesium supplementation for supportive treatment in patients with COVID-19", European Journal of Pharmacology, Elsevier Science, NL, vol. 886, Sep. 12, 2020 (Sep. 12, 2020), XP086288713, ISSN: 0014-2999, DOI: 10.1016/J.EJPHAR.2020.173546.

* cited by examiner

IRON SUPPLEMENT COMPOSITIONS AND METHODS OF USE THEREOF

CROSS REFERENCE TO RELATED APPLICATIONS

This application is a divisional of U.S. application Ser. No. 17/889,244, filed on Aug. 16, 2022, which is a continuation of International Application No. PCT/US22/40429, filed on Aug. 16, 2022, which claims priority to U.S. Provisional Patent Application No. 63/233,682, filed on Aug. 16, 2021, the contents of which are incorporated herein by reference in their entireties.

BACKGROUND

Anemia is a condition in which the blood is deficient in red blood cells, in hemoglobin, or in total volume. Hemoglobin depletion can cause many debilitating symptoms, such as, extreme fatigue, weakness, pale skin, chest pain, fast heartbeat, shortness of breath, headache, dizziness or lightheadedness, cold hands and feet, inflammation or soreness of the tongue, brittle nails, unusual cravings for non-nutritive substances (such as ice, dirt, or starch), and poor appetite (especially in infants and children with iron deficiency anemia). Anemia is a prevalent issue in elder population where above normal blood pressure levels is also a prevalent issue. Other high-risk groups include pregnant women, women of reproductive age, non-Hispanic blacks, and Hispanics.

Iron-deficiency anemia (IDA) occurs when the iron deficiency is sufficient to reduce erythropoiesis and therefore the hemoglobin level falls. IDA may impact at early stages of life by causing growth retardation, lower cognitive abilities, lethargy and poor attention. This public health concern has stimulated the research for the development of alternative preventive solutions.

Iron deficiency is the most prevalent nutritional deficiency and the main cause of anemia. Infants less than 2 years and pregnant women being the most vulnerable groups. Globally, anemia affects 1.62 billion people (95% CI: 1.50-1.74 billion), which corresponds to 24.8% of the population (95% CI: 22.9-26.7%). The highest prevalence is in preschool-age children (47.4%, 95% CI: 45.7-49.1), with 43% of all pre-school children having anemia. The lowest prevalence is in men (12.7%, 95% CI: 8.6-16.9%). However, the population group with the greatest number of individuals affected is non-pregnant women (468.4 million, 95% CI: 446.2-490.6).

| | Prevalence of anaemia | | Population affected | |
|---|---|---|---|---|
| | | | Number | |
| Population group | Percent | 95% CI | (millions) | 95% CI |
| Preschool-age children | 47.4 | 45.7-49.1 | 293 | 263-303 |
| School-age children | 25.4 | 19.9-30.9 | 305 | 238-371 |
| Pregnant women | 41.8 | 39.9-43.8 | 56 | 54-59 |
| Non-pregnant women | 30.2 | 28.7-31.6 | 468 | 446-491 |
| Men | 12.7 | 8.6-15.9 | 260 | 175-345 |
| Elderly | 23.9 | 18.3-29.4 | 164 | 126-202 |
| Total population | 24.8 | 22.9-26.7 | 1620 | 1500-1740 |

Because anemia hinders the blood's ability to carry oxygen, it can severely affect pregnant women and children. In the current time of the COVID-19 pandemic, anemia is a dangerous comorbidity in pregnant women and children. Damage from anemia may be permanent and lead to the development of neoplastic processes, diabetes, cardiovascular disease.

Daily iron supplementation has been proposed as an effective remedy for older children and pregnant women, but evidence of such an effect in infants' iron deficiency is scarce. Iron supplementation is recommended as a priority strategy and has been endorsed by the World Health Organization (WHO) when the prevalence of iron deficiency is high in a specific population. Pediatric societies around the world recommend daily ferrous sulfate supplementation in infants less than 4 months of age receiving formula and from 6 months onwards in breastfed infants. Despite this recommendation and the free supply of ferrous sulfate, adherence is low, mainly due to gastrointestinal adverse effects, mothers' neglect, and low rate of prescription by healthcare team members. Additionally, there are health risks to having too much iron. Excess iron, for example from over supplementation, may cause genomic instability and thereby resulting in structural and functional alterations in proteins, lipids, and DNA. Thus, although, weekly ferrous sulfate supplementation has been proposed as an alternative preventive treatment for IDA since the nineties, the need for a safe and effective iron supplementation formulation is still great and remains unanswered.

Iron deficiency can also arise from blood donation. Blood donation results in a substantial loss of iron (200 to 250 mg) at each bleeding procedure (425 to 475 ml) and subsequent mobilization of iron from body stores. Recent reports have shown that body iron reserves generally are small and iron depletion is more frequent in blood donors than in non-donors. The lost amount of hemoglobin recovered after blood donation is usually recovered after a mean of 36±11 days. Iron supplementation, in the form of usual iron salts, such as iron sulfate, can shorten the time of hemoglobin recovery to 32 days, but that benefit is minor. Thus, there is a need for an improved iron supplement formulation that can replete the body's stored hemoglobin rapidly, especially after blood donation.

SUMMARY

Described herein is an iron supplement composition comprising elemental metal iron and a source of nitrate anion ($NO_3^-$). The term "elemental metal iron" refers to elemental iron or iron in its metallic, uncharged, elemental form. The term "elemental metal iron" does not refer to any charged form of iron, such as iron oxides, iron salts, iron hydroxides, or iron hydrides. In some aspects, the source of nitrate anion is a salt of nitric acid or salt of nitrous acid, for example, potassium nitrate, sodium nitrate, magnesium nitrate, potassium nitrite, sodium nitrite, or magnesium nitrite. In other aspects, the source of nitrate anion is a botanical source, for example an *Amaranthus* extract. In certain embodiments, the amount of elemental metal iron is 10 mg and the amount of the source of nitrate anion provides 350 mg nitrate anion. In some aspects, the composition further comprises an acid, for example ascorbic acid. In some embodiments, the amount of acid is the composition is 100 mg.

In certain embodiments, the composition is in the dosage form of a capsule, a cachet, a pill, a tablet, a powder, a granule, a pellet, a bead, a particle, a troche, or a pastille. For example, the elemental metal and the source of nitrate anion are in separate dosage forms. In other implementations, the elemental metal and the source of nitrate anion are packaged in a capsule, a cachet, a pill, a tablet, a powder, a granule, a pellet, a bead, a particle, a troche, or a pastille. In certain embodiments, the acid is packaged separately from the source of nitrate anion and the elemental metal. In some aspects, the source of nitrate anion, the elemental metal, and the acid are in solid forms.

Also described are methods of iron supplementation, for example, methods of replenishing iron and/or ferritin in a subject or methods of replenishing hemoglobin storage in a subject. In some aspects, the subject is diagnosed with anemia, low blood iron level, low ferritin level, and/or low hemoglobin levels. In some implementations, the subject exhibits at least one symptom selected from the group consisting of: extreme fatigue, weakness, pale skin, chest pain, fast heartbeat, shortness of breath, headache, dizziness or lightheadedness, cold hands and feet, inflammation or soreness of the tongue, brittle nails, unusual cravings for non-nutritive substance, and poor appetite. Also described are methods of replenishing blood iron level, ferritin level, and/or hemoglobin levels in a subject, for example, after a subject a suffer has suffered a blood loss incident, which includes a blood donation. These methods comprise administering to a subject the iron supplement composition described herein.

Thus, the method comprises orally administering an effective amount of elemental metal iron to the subject and orally administering an effective amount of a source of nitrate anion to the subject. In certain implementations, the effective amount of elemental metal iron is 1-100 mg. The effective amount of nitrate anion is 30-4000 mg. In some aspects, the method also comprises orally administering an effective amount of an acid in the subject. The effective amount of the acid is 10-5000 mg.

In some implementations, the effective amount of the elemental metal iron is 0.3-45 μmol/kg body weight and the effective amount of the nitrate anion is 0.008-1.6 mmol/kg body weight. Where the acid is ascorbic acid, the effective amount of the acid is 0.001-0.7 mmol/kg body weight. In a particular embodiment, the effective amount of the elemental metal iron is 0.0032 mmol/kg body weight, the effective amount of the nitrate anion is 0.1000 mmol/kg body weight, and the effective amount of the ascorbic acid is 0.0101 mmol/kg body weight.

DETAILED DESCRIPTION

Detailed aspects and applications of the disclosure are described below in the following detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant art, that implementations of the technology disclosed herein may be practiced without these specific details. It should be noted that there are many different and alternative configurations, devices, and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the term "about" refers to a deviation no more than 5% of the given value, for example a deviation of 3%, 2%, 1%, 0.5%, or 0.1% of the given value.

As used herein, the term "acceptable" is a phrase used in its broadest sense and may describe ingredients of a composition that meet Food and Drug Administration (FDA) standards, United States Pharmacopeia (USP) standards, US Department of Agriculture (USDA) standards for food-grade materials, commonly accepted standards of the nutritional supplement industry, industry standards, botanical standards, or standards established by any individual. These standards may delineate acceptable ranges of aspects of ingredients of a composition such as edibility, toxicity, pharmacological effect, or any other aspect of a chemical, composition, or preparation used in implementations of a composition.

As used herein, the term "composition" refers to both a mixture of ingredients or constituents as well as a combination of capsules that contains different ingredients or constituents. Accordingly, in certain embodiments, a composition encompasses separate capsules that are packaged together and are meant to be taken together.

As used herein, the term "elemental metal iron" refers to the neutral-charged state of iron, in other words, iron in its elemental form and not in a salt form or charged form (exemplary salt forms and charged forms include the oxide, hydroxide, carbonate, chloride, lactate, citrate, aspartate, glycinate, and gluconate of the metal). Thus, the term "elemental metal iron" does not refer to iron oxides, iron salts, iron hydroxides, or iron hydrides.

As used, herein, the term "subject" refers to a mammal, e.g., a human, mouse, rat, guinea pig, dog, cat, horse, cow, pig, or non-human primate, such as a monkey, chimpanzee, baboon, or rhesus.

The present disclosure relates to the discovery that a composition comprising elemental metal iron can improve a body's hemoglobin stores, contrary to the iron supplement products available today. The composition comprises elemental metal iron, a source of nitrate anion, and an acid. In some embodiments, the composition comprises 1-100 mg elemental metal iron, 30-4000 mg nitrate anion, and 10-5000 mg acid. In some implementations, the composition further comprises a source of folate and is can be tolerated by a pregnant subject, which can save the lives and health of millions of mothers and fetuses. In certain embodiments, the source of nitrate anion is a nitrate salt, for example potassium nitrate. In other embodiments, the source of nitrate anion is a botanical source, for example an extract of a green leafy vegetable or a plant containing high levels of nitrate such as beetroot or *Amaranthus*.

In some embodiments, the composition comprises about 10 mg elemental metal iron and an amount of the source of nitrate anion ($NO_3^-$) that provides about 350 mg nitrate anion. The elemental metal iron may be in any form, for example, a powder or granules. In certain embodiments, the nitrate anion is provided by a botanical source, for example, an *Amaranthus* extract. In particular embodiments, the composition comprises about 10 mg elemental metal iron and an amount of extract from *Amaranthus dubius* and *Amaranthus tricolor* that provides about 350 mg nitrate anion ($NO_3^-$). In some aspects, the composition further comprises about 100 mg of an acid, for example ascorbic acid.

In other embodiments, the composition comprises about 16.7 mg elemental metal iron and about 255 mg nitrate anion ($NO_3^-$). In some aspects, such compositions further comprise a source of folate (for example, 5-methyltetrahydrofolate, 5-MTHF) and an acid. In particular embodiments, the composition further comprises about 5 mg 5-MTHF (or the equivalent of about 3 mg folate, according to the FDA-accepted conversion factor of 1.7) and about 833 mg ascorbic acid. In certain implementations, the nitrate anion ($NO_3^-$) is provided in the form of a nitrate salt, for example potassium nitrate. Accordingly, in certain embodiments, the composition comprises about 16.66 mg elemental metal iron, about 416 mg potassium nitrate, about 833 mg ascorbic acid, and about 5 mg 5-MTHF.

The disclosed composition may be in the form of a capsule, tablet, pill, liquid, liquid suspension, vapor, powder, granulate, pulverulence, or a combination thereof. In a preferred embodiment, the disclosed composition is in a solid form. In certain implementations the composition is provided via a plurality of a capsule, a cachet, a pill, a tablet, a powder, a granule, a pellet, a bead, a particle, a troche, or a pastille. In some embodiments, the elemental metal iron and the source of nitrate anion ($NO_3^-$), and in some aspects the acid, are combined into one capsule or one tablet. In other embodiments, the acid is in a separate tablet or capsule than the elemental metal iron and the source of the nitrate ion. The enhanced activity of co-administration the source of nitrate anion ($NO_3^-$) and the elemental metal iron are not reduced if the subject ingests the source of nitrate anion ($NO_3^-$) and the elemental metal iron separately, for example via co-administration of separate capsules of the source of nitrate anion ($NO_3^-$) and the elemental metal iron.

Accordingly, in some aspects, the composition described herein comprises a capsule comprising a source of nitrate anion ($NO_3^-$) and a capsule comprising an elemental metal iron. In another embodiment, the composition is in a capsule comprising about 2.5 mg elemental metal iron and an amount of the source of nitrate anion ($NO_3^-$) that provides about 87.5 mg nitrate anion. In embodiments of the composition further comprising an acid, the composition further comprises a capsule comprising the acid. Accordingly, in some embodiments, the composition is a capsule, a cachet, a pill, a tablet, a pellet, a troche, or a pastille that comprises about 2.5 mg elemental metal iron, an amount of the source of nitrate anion that provides about 85.7 mg nitrate anion, and about 25 mg acid.

In some embodiments, the elemental metal iron in the composition is covered or microencapsulated with a suitable material that is poorly soluble in water but soluble in the acidic environment of the stomach, for example, magnesium oxide, cellulose polymers, alginates (such as calcium alginate), or aluminum hydroxide.

In some aspects, the composition further comprises a suitable pharmaceutically acceptable coating (to prevent moisture from getting into the tablets) and/or an additive. Non-limiting examples of the pharmaceutically acceptable coating include waxes, polymers, solid fatty acids, etc. Non-limiting examples of the additive include a carrier, excipient, binder, colorant, flavoring agent, preservative, buffer, diluent, and combinations thereof. In some aspects, the additive is a pharmaceutically acceptable additive or an acceptable food additive.

As shown in the examples, ingestion of the composition optimizes the body's circulation, for example, by repleting the body's storage of iron and hemoglobin. The restoration of blood iron and hemoglobin levels can occur within 24 hours of the administration of the composition. Thus, also described herein are methods of iron supplementation, for example, by replenishing iron and/or hemoglobin storage in a subject. In some aspects, the subject is diagnosed with anemia, low blood iron level, low ferritin level, and/or low hemoglobin levels. In some implementations, the subject exhibits at least one symptom selected from the group consisting of: extreme fatigue, weakness, pale skin, chest pain, fast heartbeat, shortness of breath, headache, dizziness or lightheadedness, cold hands and feet, inflammation or soreness of the tongue, brittle nails, pica (unusual cravings for non-nutritive substance), and poor appetite. Also described are methods of replenishing blood iron level, ferritin level, and/or hemoglobin levels in a subject, for example, after a subject has suffered a blood loss incident. In some aspects, the blood loss incident is a blood donation.

The oral and parental iron supplement formulations commonly used today involve a plethora of gastrointestinal side effects, such as diarrhea, stomach pain, heartburn, nausea, vomiting, black stools, and constipation. However, iron supplementation using the elemental metal iron compositions disclosed herein cause the subject to experience less gastrointestinal side effects. As shown in the examples, the subjects did not report any, let alone gastrointestinal, side effects associated with iron supplementation when they ingested the disclosed composition comprising elemental metal iron. In particular, the subject who previously did experience such side effects with an iron supplement comprising iron salts reported that she did not experience any of those side effects with the disclosed composition comprising elemental metal iron. This is particularly surprising since ingestion of nitrate salts has been well-documented to cause gastrointestinal irritation (See Berge et al., "Pharmaceutical Salts, Review Article," *J Pharm Sci.*, 1977, 66(1): 1-19). In fact, The Handbook of Pharmaceutical Salts explicitly recommends that nitrate salts should not be considered for pharmaceuticals used internally (see page 298 of Stahl, P. H., Wermuth, C. G. 2002. *Handbook of pharmaceutical salts: Properties, selection, and use*. Weinheim: VHCA). Instead, the subject reported that oral co-administration of elemental metal iron and a nitrate salt did not lead to any gastric distress.

In certain implementations, the method of replenishing blood iron level, ferritin level, and/or hemoglobin levels in a subject comprises administering to the subject an effective amount of elemental metal iron, an effective amount of nitrate anion, and, in some aspects, an effective amount of an acid. In certain embodiments, the source of nitrate anion is a nitrate salt, for example potassium nitrate. In other embodiments, the source of nitrate anion is a botanical source, for example an extract of a green leafy vegetable or a plant containing high levels of nitrate such as beetroot or *Amaranthus*. In some embodiments, the acid is ascorbic acid. The effective amount of elemental metal iron is about 1 mg to about 100 mg. The effective amount of nitrate anion is about 30 mg to about 4000 mg. The effective amount of the acid is about 10 mg to about 5000 mg. In some aspects, the molar ratio of the effective amount of elemental metal iron, nitrate anion, and acid is 1:5.2:0.5 to 1:28.75:3.

In some implementations, the effective amount of the elemental metal iron is 0.3-45 μmol/kg body weight, for example, 0.4-45 μmol/kg body weight, 0.3-32 μmol/kg body weight, 0.4-32 μmol/kg body weight, 0.3-30 μmol/kg body weight, 0.4-30 μmol/kg body weight, 1.5-4.8 μmol/kg body weight, 1.5-3.2 μmol/kg body weight, or 3.2-4.8 μmol/kg body weight. In certain embodiments, the effective amount of the elemental metal iron is 0.002-0.0025 mmol/kg body weight, 0.003-0.0024 mmol/kg body weight, 0.004-0.022 mmol/kg body weight, 0.005-0.020 mmol/kg body weight, or 0.007-0.030 mmol/kg body weight.

In some implementations, the effective amount of the nitrate anion is 0.008-1.6 mmol/kg body weight, for example, 0.008-1.5 mmol/kg body weight, 0.008-1.2 mmol/ kg body weight, 0.01-1.6 mmol/kg body weight, 0.01-1.5 mmol/kg body weight, or 0.01-1.2 mmol/kg body weight. In certain embodiments, the effective amount of the nitrate anion is 0.05-1.0 mmol/kg body weight, 0.07-1.0 mmol/kg body weight, 0.08-1.0 mmol/kg body weight, 0.9-1.0 mmol/kg body weight, or 0.1-1.0 mmol/kg body weight, 0.05-0.12 mmol/kg body weight, 0.07-0.115 mmol/kg body weight, 0.08-0.125 mmol/kg body weight, 0.9-0.12 mmol/kg body weight, or 0.1-0.11 mmol/kg body weight.

Where the acid is ascorbic acid, the effective amount of the acid is 1.0-700 μmol/kg body weight, for example, 1.0-680 μmol/kg body weight, 1.0-510 μmol/kg body weight, 1.0-500 μmol/kg body weight, 1.3-700 μmol/kg body weight, 1.3-680 μmol/kg body weight, 1.3-510 μmol/kg body weight, 1.3-500 μmol/kg body weight. In certain embodiments, the effective amount of the ascorbic acid is 0.005-0.015 mmol/kg body weight, 0.007-0.013 mmol/kg body weight, 0.009-0.012 mmol/kg body weight, 0.01-0.012 mmol/kg body weight, 0.005-0.15 mmol/kg body weight, 0.007-0.13 mmol/kg body weight, 0.009-0.12 mmol/kg body weight, or 0.01-0.12 mmol/kg body weight.

In particular implementations, the effective amount of the elemental metal iron is 0.0032 mmol/kg body weight, the effective amount of the nitrate anion is 0.1000 mmol/kg body weight, and the effective amount of the ascorbic acid is 0.0101 mmol/kg body weight. In other implementations, the effective amount of the elemental metal iron is 0.0073 mmol/kg body weight, the effective amount of the nitrate anion is 0.1000 mmol/kg body weight, and the effective amount of the ascorbic acid is 0.115 mmol/kg body weight.

In some aspects, the effective amount of the elemental metal iron administered is 2.78-3.59 μmol/kg body weight; the effective amount of the nitrate anion administered is 86.8-113 μmol/kg body weight; and the effective amount of the ascorbic acid administered is 8.77-114 μmol/kg body weight.

In some aspects, the amount of element iron administered is the Recommended Dietary Allowance (RDA). For all ages of men and for postmenopausal women, the amount of elemental metal iron administered is 8 mg/day, which corresponds to about 143 μmol/day. Given that the average weight for American men is about 90 kg, the amount of elemental administered according to the described method may be 1.59-1.61 μmol/kg body weight when the subject is an adult male. Given that the average weight for American postmenopausal women is about 80 kg, the amount of elemental metal iron administered according to the described method may be 1.79-1.81 μmol/kg body weight when the subject is postmenopausal. The RDA for premenopausal women is 18 mg/day, which corresponds to about 322 μmol/day. Given that the average weight for American premenopausal women is about 77 kg, the amount of elemental metal iron administered according to the described method may be 4.16-4.18 μmol/kg body weight when the subject is premenopausal.

The disclosed method of replenishing blood iron level, ferritin level, and/or hemoglobin levels results in reduced gastrointestinal side effects (for example, diarrhea, stomach pain, heartburn, nausea, vomiting, black stools, and constipation) compared to conventional forms of iron supplementation, such as through oral administration of an iron salt. In some aspects, the subject experiences no side effects from the disclosed method of replenishing blood iron level, ferritin level, and/or hemoglobin levels.

EXAMPLES

The disclosure is further illustrated by the following examples that should not be construed as limiting. The contents of all references, patents, and published patent applications cited throughout this application, as well as the Figures, are incorporated herein by reference in their entirety for all purposes.

Example 1

One dose of the exemplary iron composition comprises 10 mg elemental metal iron, 350 mg nitrate anion, and 100 mg ascorbic acid. The dose is administered by ingestion of four gelatin capsules. Accordingly, each capsule contains 2.5 mg elemental metal iron, 87.5 mg nitrate anion, and 25 mg ascorbic acid. For subjects below average in weight, the dose for administration could be reduced to two or three gelatin capsules.

Example 2

The hemoglobin level of a healthy Caucasian subject (40 years old male, 240 lbs) was measured using a 3-in-1 Easytouch Glucose Cholesterol Hemoglobin Monitor. The detected hemoglobin level was 16.0 g/dL, which falls within the normal range. The normal range of hemoglobin level is 3.5 to 17.5 g/dl for men and 12.0 to 15.5 g/dl for women.

The next afternoon, the subject donated one pint blood to the Red Cross. His hemoglobin levels decreased by 4.375% to 15.3 g/dL. The subject ingested one dose of the iron composition described in Example 1 with one glass of water (volume about 330 ml) after having donated blood. The next morning, the subject's hemoglobin level rose to 17.3 g/dL.

During the course of one evening, the iron supplement composition replenished and increased the subject's original hemoglobin levels when compared to the level before blood donation. This is the first observation of an iron supplement that could increase hemoglobin level (by 13%) within one day after blood donation, from 15.3 g/dL to 17.3 g/dL.

Example 3

A pregnant female subject (40 years old, Jewish ancestry) exhibited symptoms of iron/hemoglobin deficiency. She exhibited symptoms of fatigue, weakness, pale or yellowish skin, irregular heartbeats, shortness of breath, dizziness or lightheadedness, chest pain, cold hands and feet and headache. She had previously given birth to 8 healthy children and never before experienced low iron levels. The subject tried various medicine and supplements comprising various iron salts but had to stop due to severe gastrointestinal disturbances (for example, stomach pain, heartburn, constipation, diarrhea, black stools, and nausea). Her blood was tested using a 3-in-1 Easytouch Glucose Cholesterol Hemoglobin Monitor, and the measured hemoglobin level was diagnosed as low (<7).

The patient was given a formulation comprising 833 mg of ascorbic acid, 416 mg potassium nitrate, and 16.66 mg of elemental metal iron. The subject was advised to ingest the capsules of the formulation once in the morning on an empty stomach with 500 mg cold water.

The average mesh size of the elemental metal iron was 325. The size was selected based on these iron particles dissolving under the effect of the stomach acid and the ascorbic acid in the formula slowly, which would minimize any of the GI side effects. As the subject is pregnant, a source of folate was added to the formulation as folate is highly needed for both healthy fetal development and proper hemoglobin differentiation. Given her lackluster of response to the previous iron supplementation regime, 5-MTHF (5 mg) was added the formulation instead of folate in case she lacks the ability to metabolize folic acid to 5-MTFH which is necessary for hemoglobin formation.

After five days of ingesting the formulation as advised, the patient reported noticeable improvement in feelings of well-being and health. She also reported an end to the symptoms of anemia and that she did not experience any of the GI side effects associated with her previous iron supplementation regime. Her blood hemoglobin levels were tested again after five days of supplementation, and it increased to 12.4, which is well within the normal range for a pregnant woman.

We claim:

1. A method of replenishing a human subject's iron, ferritin, and/or hemoglobin level, the method comprising:
- orally administering elemental metal iron to the subject; and
- orally administering a source of nitrate anion to the subject.

2. The method of claim 1, wherein the source of nitrate anion is a nitrate salt.

3. The method of claim 2, wherein the source of nitrate anion is potassium nitrate.

4. The method of claim 1, wherein the source of nitrate anion is a botanical source.

5. The method of claim 4, wherein the botanical source is an *Amaranthus* extract or beetroot extract.

6. The method of claim 1, wherein the elemental metal iron has a mesh size of 325.

7. The method of claim 1, further comprising orally administering an acid to the subject.

8. The method of claim 7, wherein the subject is orally administered a composition comprising the elemental metal iron; source of nitrate anion; and the acid.

9. The method of claim 1 wherein the subject is diagnosed with anemia, low blood iron level, low ferritin level, and/or low hemoglobin levels.

10. The method of claim 9, wherein the subject exhibits at least one symptom selected from the group consisting of: extreme fatigue, weakness, pale skin, chest pain, fast heartbeat, shortness of breath, headache, dizziness, lightheadedness, cold extremities, tongue inflammation, tongue soreness, brittle nails, pica, and poor appetite.

11. The method of claim 9, wherein the subject's hemoglobin level is reduced from donating blood.

12. The method of claim 1, wherein the subject has donated blood.

13. The method of claim 12, wherein the subject's hemoglobin level is lower than that before donating blood.

14. The method of claim 1, where the subject exhibits reduced gastrointestinal side effect compared to oral administration of iron salts or elemental metal iron alone.

15. The method of claim 14, wherein the gastrointestinal side effect is at least one side effect selected from the group consisting of: diarrhea, stomach pain, heartburn, nausea, vomiting, black stools, and constipation.

16. The method of claim 1, wherein the subject is administered 10 mg elemental metal iron and 87.5 mg nitrate anion, the method further comprising orally administering 100 mg ascorbic acid to the subject.

17. The method of claim 1, wherein the subject is administered 0.004-0.22 mmol elemental metal iron/kg body weight and 0.08-1.2 mmol nitrate anion/kg body weight.

18. The method of claim 17, wherein method further comprises orally administering to the subject 0.009-0.12 mmol ascorbic acid/kg body weight.

19. The method of claim 18, wherein the subject is administered 0.0032 mmol elemental metal iron/kg body weight, 0.1000 mmol nitrate anion/kg body weight, and 0.0101 mmol ascorbic acid/kg body weight.

20. A method of increasing oral bioavailability of elemental metal iron in a human subject, the method comprising:
- orally administering elemental metal iron to the subject; and
- orally administering a source of nitrate anion to the subject, wherein the elemental metal iron and the source of nitrate anion are co-administered.

21. The method of claim 20, wherein the nitrate anion is of a botanical source, wherein the botanical source is an *Amaranthus* extract or beetroot extract.

22. The method of claim 20, wherein the elemental metal iron has a mesh size of 325.

23. The method of claim 20, further comprising orally administering an acid to the subject.

24. The method of claim 23, wherein the acid is co-administered with the elemental metal iron and the source of nitrate anion.

25. The method of claim 24, wherein the subject is orally administered a composition comprising the elemental metal iron; the source of nitrate anion; and the acid.

26. The method of claim 1, where the subject exhibits no side effects from oral administration of the elemental metal iron and the source of nitrate anion.

27. The method of claim 20, wherein the source of nitrate anion is a botanical source.

* * * * *